United States Patent [19]

Satterthwaite

[11] Patent Number: 4,907,575
[45] Date of Patent: Mar. 13, 1990

[54] AMBULATORY LUMBAR TRACTION DEVICE

[76] Inventor: H. Sherwood Satterthwaite, 2005 Beechwood Rd., Hyattsville, Md. 20783

[21] Appl. No.: 227,549

[22] Filed: Aug. 3, 1988

[51] Int. Cl.$^4$ .............................................. A61H 1/02
[52] U.S. Cl. ....................................... 128/75; 128/78; 128/84 R
[58] Field of Search ...................... 128/69, 71, 75, 78, 128/84 R, 85, 92 R

[56] References Cited

U.S. PATENT DOCUMENTS

| | | | |
|---|---|---|---|
| 2,162,189 | 6/1939 | Williams | 128/78 |
| 2,166,229 | 7/1939 | Anderson | 128/84 R |
| 2,687,129 | 8/1954 | Talkish | 128/78 |
| 2,871,850 | 2/1959 | Peckham | 128/78 |
| 2,886,031 | 5/1959 | Robbins | 128/78 |
| 3,029,810 | 4/1962 | Martin | 128/78 |
| 3,177,869 | 4/1965 | Bartels | 128/75 |
| 3,420,230 | 1/1969 | Ballard | 128/75 |
| 3,548,817 | 12/1970 | Mittasch | 128/75 |
| 3,716,049 | 2/1973 | Kaplan | 128/75 |
| 3,889,664 | 6/1975 | Heuser et al. | |
| 4,372,552 | 2/1983 | Carlmark | 128/75 |
| 4,715,362 | 12/1987 | Scott | 128/75 |

Primary Examiner—Robert A. Hafer
Assistant Examiner—Charles H. Sam
Attorney, Agent, or Firm—Jerome J. Norris

[57] ABSTRACT

Ambulatory traction device for reducing body weight on lumbo-sacral area of spine comprising: upper support for encircling upper body region; lower support for placement on sides above the hips, and at least two turnbuckles extending vertically between the upper and lower supports and having end rods fixed to rigid innermost plates sandwiched inside of soft and pliable parts of the upper and lower support members.

5 Claims, 1 Drawing Sheet

AMBULATORY LUMBAR TRACTION DEVICE

FIELD OF THE INVENTION

The present invention relates to a novel traction device for providing traction to eliminate or reduce upper body weight forces on the discs of the vertebral or other bone or cartilage in the lumbar, sacral or pelvic area, while simultaneously allowing a patient to be ambulatory or free from confinement to a bed, as normally required with known back traction devices.

BACKGROUND OF THE INVENTION

In general, typical prior art lumbo-sacral traction devices for alleviating or minimizing the compressive weight on vertebral discs, cartilage or the bone configuration in the lumbar, sacral or pelvic area, from the upper body weight during injury, encumbered the patient. The patient was encumbered because these devices required the patient to be either confined in bed or to some other restriction, which did not afford freedom of movement to perform normal activities or to be productive.

Because of the non-ambulatory nature of these generally well known prior art traction devices, the recovery period was both frustrating and unproductive for the patient, and these disadvantages often times caused him to attempt to return to normal activities earlier than warranted, with the attendant consequences of reinjuring himself and requiring further and longer confinement to the restrictive traction device than was contemplated at commencement of the treatment.

The novel ambulatory lumbar traction device of the present invention is free from prior art traction device strictures which required the patient to be confined in bed with cables attached to parts of his body and weights or sand bags fixed to the cables in order to create tension to reduce compressive forces normally present upon the lumbo-sacral region.

As a result of the advance made via the ambulatory lumbar traction device of the invention, a patient undergoing traction treatment using the device has the freedom to use more than just his arms, because the ambulatory range allowed by the device does not require the patient to be confined by a vertically disposed or upright lumbo-sacral traction system attached to a chair, as disclosed in U.S. Pat. No. 3,167,068.

SUMMARY OF THE INVENTION

One object of the present invention is to provide a novel lumbar traction device which permits a patient undergoing traction treatment to have freedom of movement except in the area of the lumbo-sacral region where traction is being applied.

Another object of the invention is to provide a new lumbar traction device which does not confine a patient to a bed and which does not confine a patient to a chair, as in the case of an upright lumbo-sacral traction device.

A yet further object of the invention is to provide a novel lumbar traction device which allows a patient undergoing traction treatment to be completely ambulatory during the treatment, and to have complete freedom of movement of his limbs.

The novel traction device for the back or lumbar region comprises a lower support member disposed for placement on the sides and above a patient's hips, a horizontally encircling removably fastenable upper support member contoured to fit about an area of the upper body adjacent to the Trapezius, Latissimus dorsi, and Pectoralis major muscles, and at least a pair of vertically disposed longitudinally adjustable turn buckles having rod ends which are permanently fixed to rigid interior plate members which are sandwiched inside of soft and pliable parts of the lower and upper support members.

DETAILED DESCRIPTION OF THE INVENTION

Figure 1:
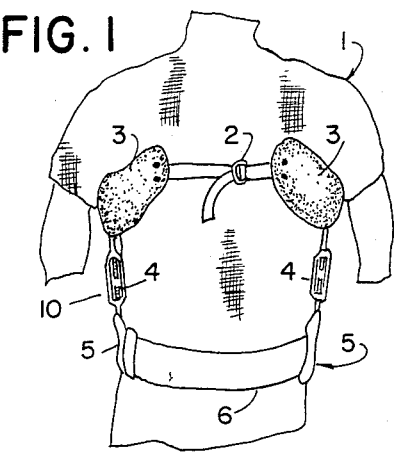
FIG. 1 is a front view of the traction device in accordance with the invention, attached to body areas of a patient to create traction.
Figure 2:
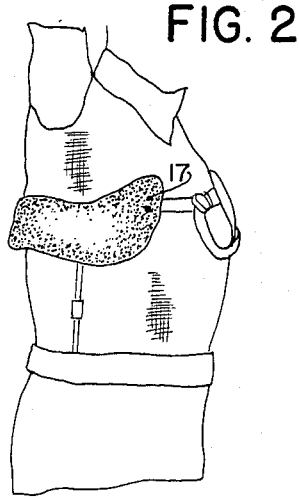
FIG. 2 is a side view of the traction device of the invention attached to areas of the body of a patient to create traction, wherein the lower support member is covered by the patient's belt.
Figure 6:
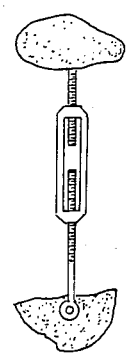
FIG. 6 is an enlarged view of the turnbuckle element.

In referring to FIG. 1, there is shown a traction device 10. In accordance with the requirements of the invention and in position around a patient's body, designated by numeral 1. The traction device consists, in part, of two lengths of straps (designated by the numeral 2.) One length of strap is attached to the end of the left upper support (identified by the numeral 3) and the other length of strap is attached to the end of the right upper support (identified by the numeral 3) by rivets (identified by the numeral 17). The upper supports go horizontally around the back, under the arms and curve upwardly and inwardly to fit snugly when pulled tightly and fastened, as by a buckle, velcro surfaces or other known fastening means, about and adjacent to the trapezius, latissimus dorsi and pectoralis major muscles.

Figure 3:
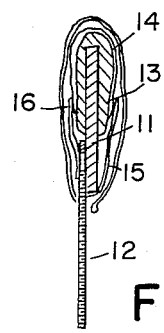
FIG. 3 is a partial view in longitudinal or vertical section of the upper support member of the traction device.
Figure 4:
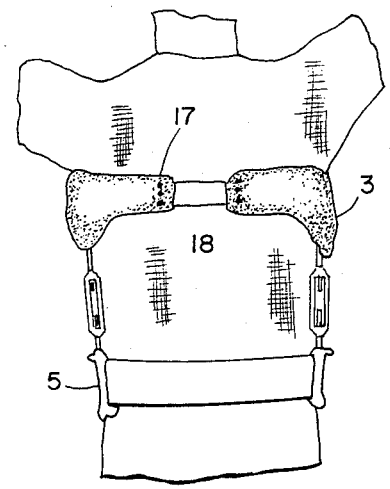
FIG. 4 is a back view of the traction device in accordance with the invention, attached to a patient's body.
Figure 5:
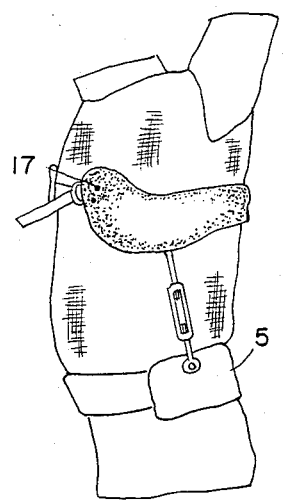
FIG. 5 is a side view of the traction device of the invention, attached to areas of the body of a patient to create traction, wherein the lower support member is not covered.

It has been found that, to allow substantially complete circulation as well as a comfortable fit in the area bounded by both the upper and lower support members, while ensuring sufficient integrity and constancy of traction, the innermost part of the support members should be a rigid plate which is made of a plastic such as teflon, as shown by reference numeral 11, in FIG. 3.

Rod 12 of the turnbuckle is riveted to the teflon innermost plates in both the upper and lower support members, and this connection enables the traction force to remain constant when the turnbuckle link is adjusted to a given level of traction, after the device is fixed about the body. Foam rubber 13, is adhesively bound around the upper portion of the teflon plate, and a canvas covering is bound or tied over the foam rubber with a strap 15, in a manner so as to maintain it in a prestressed form.

For ease of wear as well as comfort over the body, the outer shell or covering of the support members is made of a waterproof canvas, such as Tarpaulin 16 on the inside and soft leather on the outside.

In operation, the traction device provides supplementary support for the upper body weight of the patient's body 1, because the weight of the upper body is carried by the turnbuckle-teflon plate from the upper support members 3 to the lower support members 5 by turnbuckle rods 12. As a result of this traction device, the weight from the upper body on the patient's spine can be relieved or reduced, while allowing the patient to enjoy ambulatory movement that is productive.

Utilizing the traction device of the invention, the patient is able to walk about with his hands free and can sit and stand without restrictions. Moreover, the device can be used to induce a constant traction force to the spine regardless of whether the patient is standing, sitting or lying down, and the device is adjustable. Further, because of the manner in which the support members are put together, impacts or shocks from any direction are easily absorbed or minimized while the patient is recovering from earlier injuries. And since webbing straps 2 and 18 are fixed by rivets 17, to the front and back tarpaulin covering of the upper support member, a substantial range of movement is allowed to the underlying musculature without compromising the traction induced by the turnbuckle link, when the straps are tightened.

It will be apparent to those skilled in the art that many changes can be made within the invention teaching, which has been set forth by illustrative rather than limiting embodiments, and that these changes can be made without departing from the spirit and scope of the invention, which is defined hereinafter by the claims.

What is claimed is:

1. An ambulatory traction device for eliminating or reducing the upper body weight on the lumbosacral area of a patient's spine, comprising:
   an upper support member disposed to horizontally encircle a patient about an upper body region group of muscles;
   a lower support member disposed for placement on the sides above a patient's hips; and
   at least two turnbuckles extending vertically between said upper support and said lower suport having end rods permanently fixed to rigid innermost plates sandwiched inside of soft and pliable parts of the upper and lower support members; wherein said upper support member is fixed to elastic straps and is contoured to fit snugly about and adjacent to the Trapezius, Latissimus dorsi and Pectoralis major muscles when said straps are tightened about the upper body; and wherein foam rubber is adhesively bound over a part of said innermost plate, a canvas covering is bound over said foam rubber with a strap to hold said rubber in a prestressed state, tarpulin is the inside of an outer covering of said members, and soft leather is the outside.

2. The device of claims 1, wherein said lower support member contains a belt that is leather.

3. The device of claim 2, wherein said rigid innermost plates are made of Teflon.

4. The device of claim 3, wherein said straps are riveted to said supports.

5. The device of claim 4, wherein said turnbuckle end rods are riveted to said rigid teflon plates.

* * * * *